(12) United States Patent
Huwais

(10) Patent No.: US 9,737,312 B2
(45) Date of Patent: Aug. 22, 2017

(54) FLUTED OSTEOTOME AND SURGICAL METHOD FOR USE

(71) Applicant: Huwais IP Holding LLC, Jackson, MI (US)

(72) Inventor: Salah Huwais, Jackson, MI (US)

(73) Assignee: Huwais IP Holding LLC, Jackson, MI (US)

(*) Notice: Subject to any disclaimer, the term of this patent is extended or adjusted under 35 U.S.C. 154(b) by 76 days.

(21) Appl. No.: 14/705,535

(22) Filed: May 6, 2015

(65) Prior Publication Data
US 2015/0230805 A1 Aug. 20, 2015

Related U.S. Application Data

(63) Continuation of application No. 13/608,307, filed on Sep. 10, 2012, now Pat. No. 9,028,253, which is a
(Continued)

(51) Int. Cl.
*A61B 17/16* (2006.01)
*A61C 8/00* (2006.01)

(52) U.S. Cl.
CPC ........ *A61B 17/1615* (2013.01); *A61C 8/0089* (2013.01)

(58) Field of Classification Search
CPC .................................................. A61B 17/1615
See application file for complete search history.

(56) References Cited

U.S. PATENT DOCUMENTS

| 3,556,669 A | 1/1971 | Valeska et al. |
| D269,040 S | 5/1983 | Deemer |

(Continued)

FOREIGN PATENT DOCUMENTS

| DE | 102004010859 A1 | 4/2005 |
| DE | 102004010856 A1 | 6/2005 |

(Continued)

OTHER PUBLICATIONS

Anitua, Ridge expansion with motorized drills, Implant Dialogue, 14 pgs.
(Continued)

*Primary Examiner* — David Bates
*Assistant Examiner* — Olivia C Chang
(74) *Attorney, Agent, or Firm* — Endurance Law Group PLC

(57) ABSTRACT

A surgical method and tool for expanding an initial osteotomy (42) to receive a bone implant (44). An osteotome (22) having a tapered working end (28) is inserted into the initial osteotomy (42). The initial osteotomy (42) is enlarged by simultaneously rotating and pushing the working end (28) of the tapered osteotome (22) into the osteotomy (42). When rotated in one direction the burnishing edges (40) concentrate the pushing and rotational force in outward normal and tangential component forces against the interior surface of the osteotomy (42) to incrementally expand the osteotomy (42) with little to no removal of bone material (46). When rotated in the opposite direction the burnishing edges cut the interior surface of the osteotomy. Progressively larger tapered osteotomes (22) are used until an osteotomy (42) of predetermined size is achieved.

16 Claims, 12 Drawing Sheets

Related U.S. Application Data continuation-in-part of application No. 13/427,391, filed on Mar. 22, 2012, now Pat. No. 9,022,783.

(60) Provisional application No. 61/466,579, filed on Mar. 23, 2011.

(56) References Cited

U.S. PATENT DOCUMENTS

| | | |
|---|---|---|
| 4,474,556 A | 10/1984 | Ellis et al. |
| 4,850,867 A | 7/1989 | Senia et al. |
| 5,220,964 A | 6/1993 | Deken et al. |
| 5,443,468 A | 8/1995 | Johnson |
| 5,536,127 A | 7/1996 | Pennig |
| 5,667,509 A | 9/1997 | Westin |
| 5,688,120 A | 11/1997 | Yacker et al. |
| 5,735,689 A | 4/1998 | McSpadden |
| 6,146,138 A | 11/2000 | Dalmau |
| 6,179,616 B1 | 1/2001 | Danger |
| 6,186,787 B1 | 2/2001 | Danger et al. |
| 6,561,805 B2 | 5/2003 | Kumar |
| 6,641,395 B2 | 11/2003 | Kumar et al. |
| 7,198,488 B2 | 4/2007 | Lang et al. |
| 7,241,144 B2 | 7/2007 | Nilo et al. |
| 7,247,020 B2 | 7/2007 | Takahashi et al. |
| 7,300,281 B2 | 11/2007 | Cantatore et al. |
| 7,402,040 B2 | 7/2008 | Turri |
| 7,435,086 B2 | 10/2008 | Berutti et al. |
| 7,488,327 B2 | 2/2009 | Rathbun et al. |
| 7,547,210 B1 | 6/2009 | Valen |
| D611,511 S | 3/2010 | Aldecoa |
| 7,766,657 B2 | 8/2010 | Jaunberzins |
| 2001/0019816 A1 | 9/2001 | Kumar |
| 2002/0094508 A1 | 7/2002 | Lorenzi |
| 2004/0230195 A1 | 11/2004 | Kaikkonen et al. |
| 2005/0118550 A1* | 6/2005 | Turri ................ A61B 17/1624 433/65 |
| 2005/0123364 A1 | 6/2005 | Zhou |
| 2005/0273110 A1 | 12/2005 | Boehm et al. |
| 2006/0085005 A1 | 4/2006 | Kenealy et al. |
| 2006/0111724 A1* | 5/2006 | Yeung Wai Ping .............. A61B 17/1635 606/80 |
| 2006/0121415 A1 | 6/2006 | Aldecoa |
| 2006/0127847 A1 | 6/2006 | Danger et al. |
| 2006/0210949 A1 | 9/2006 | Stoop |
| 2007/0037117 A1* | 2/2007 | Jaunberzins ........... A61C 5/023 433/102 |
| 2010/0266984 A1 | 10/2010 | Jung |
| 2010/0273128 A1 | 10/2010 | Aldecoa |
| 2010/0291511 A1 | 11/2010 | Lee |
| 2010/0297578 A1 | 11/2010 | Jaunberzins |
| 2010/0330534 A1 | 12/2010 | Hyun |
| 2012/0244497 A1 | 9/2012 | Huwais |
| 2013/0218160 A1 | 8/2013 | Bjorn et al. |

FOREIGN PATENT DOCUMENTS

| | | |
|---|---|---|
| DE | 102004010858 A1 | 6/2005 |
| DE | 102004010860 A1 | 6/2005 |
| EP | 0379201 A2 | 7/1990 |
| EP | 1273273 A2 | 1/2003 |
| EP | 2119403 A1 | 11/2009 |
| FR | 2594684 A | 8/1987 |
| JP | H10217030 | 8/1998 |
| WO | 2005011514 A2 | 2/2005 |
| WO | 2007086622 A1 | 8/2007 |
| WO | 2011053588 A1 | 5/2011 |

OTHER PUBLICATIONS

Biohorizons, VIP Catalog and Surgical Manual, 2008, 28 pgs.
Biomet Sports Medicine, Bone Dowel Harvester, Copyright 2007, Biomet Sports Medicine, Inc., PO Box 587, Warsaw, IN 46581-0587 (www.biometsportsmedicine.com).
Calvo-Guarado JL et al., "Compressive osteotomes for expansion and maxilla sinus floor lifting," Med Oral Patol Oral Cir Bucal 2006; 11:E52-5.
Goyal et al., Bone Manipulation Techniques, International Journal of Clinical Implant Dentistry, Jan.-Apr. 2009; 1(1): pp. 22-31.
Lee, Atraumatic Ridge Expansion and Implant Site Preparation with Motorized Bone Expanders, Practical Procedures and Aesthetic Dentistry 2006; 18(1): pp. A-F.
Meisinger, Bone Management catalog, pp. 161-178.
Meisinger, Split-Control, retrieved Mar. 10, 2012 from www.bone-management.com/eng/bm_sortimente_anw_split_eng.htm.
Nishioka, Bone Spreading Technique (Dec. 9, 2010), retrieved Mar. 10, 2012 from www.dentistrytoday.com/implants/4228-bone-spreading-technique, pp. 1-4.
Oxforddictionaries.com. Definition of radial [retrieved on Feb. 25, 2015]. Retrieved from the Internet:http://www.oxforddictionaries.com/us/definition/american_english/radial.
Steier et al., Better horizontal ridge expansion, Dental Tribune I, Sep. 22-28, 2008, pp. 9-10.
Summers, A New Concept in Maxillary Implant Surgery: The Osteotome Technique, Compend Contin Educ Dent, vol. XV, No. 2, pp. 152-160.
www.dentsply-friadent.com, "Ankylos Surgical Manual."
www.nobelbiocare.com, "Validating Innovation: NobelActive Technical and Clinical Story," Nobel Biocare Services AG, 2011.

\* cited by examiner

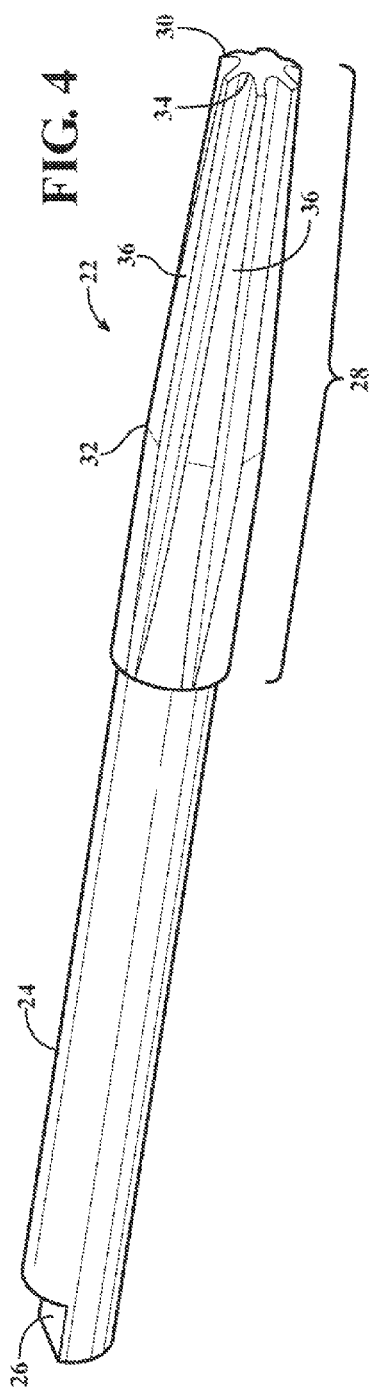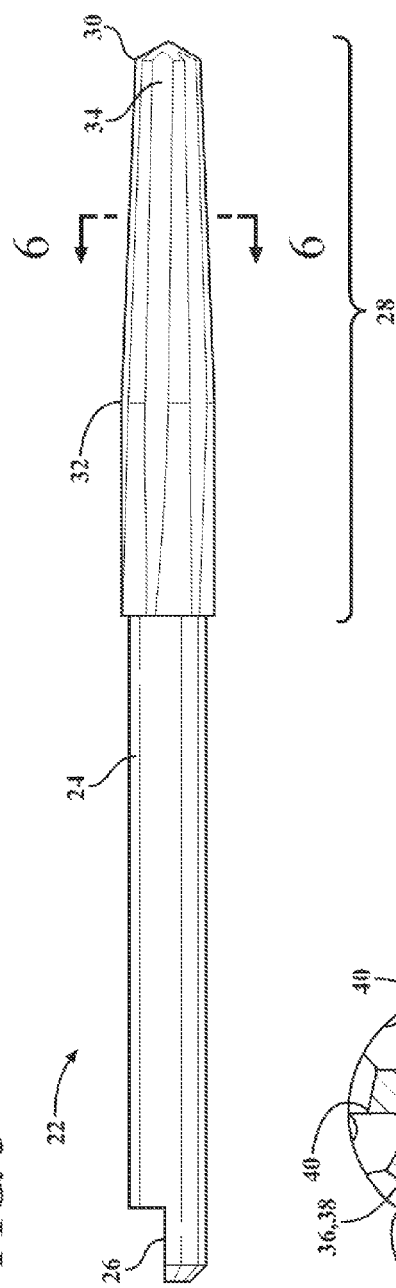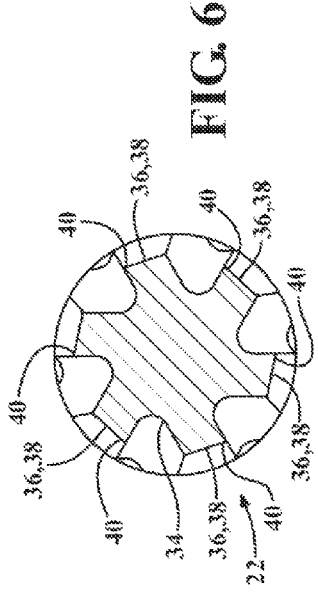

FIG. 9
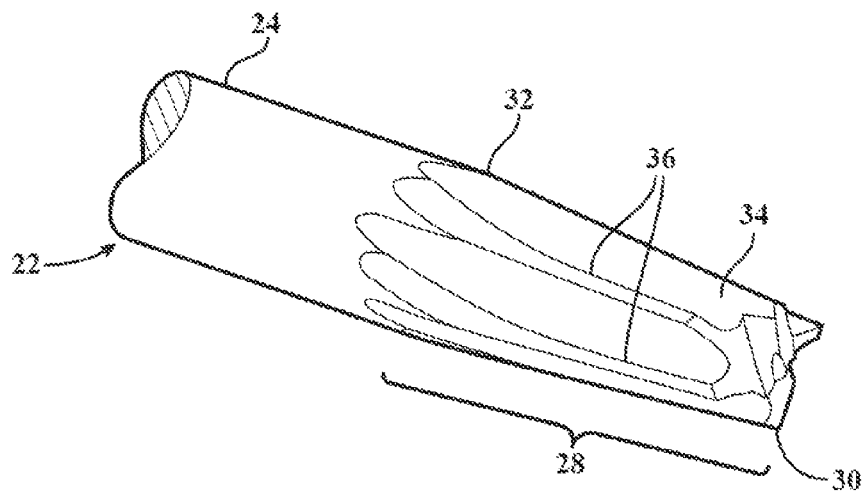
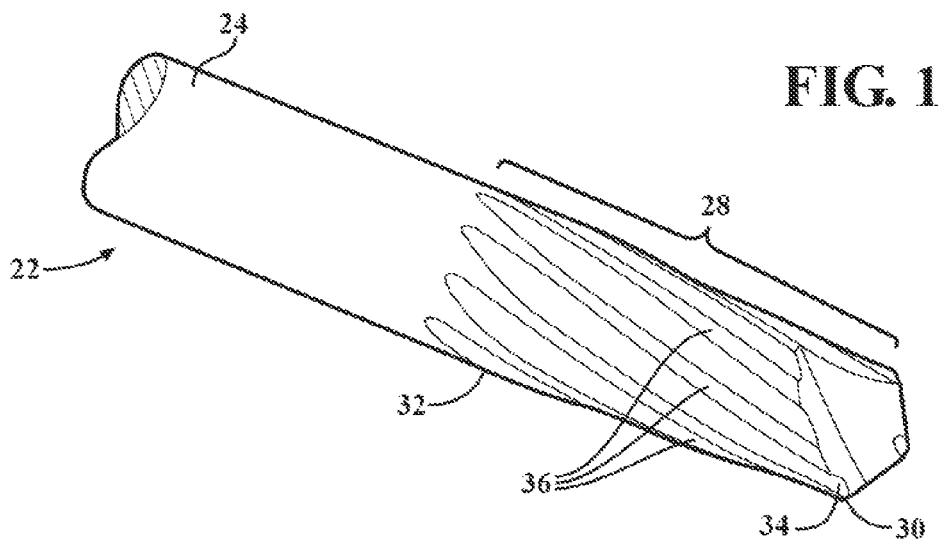
FIG. 10

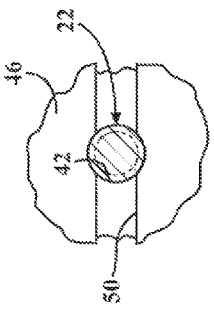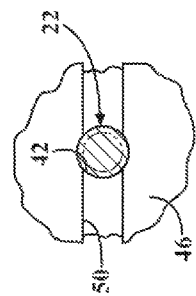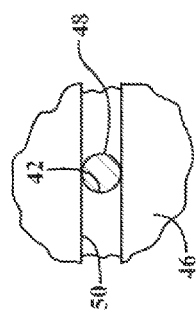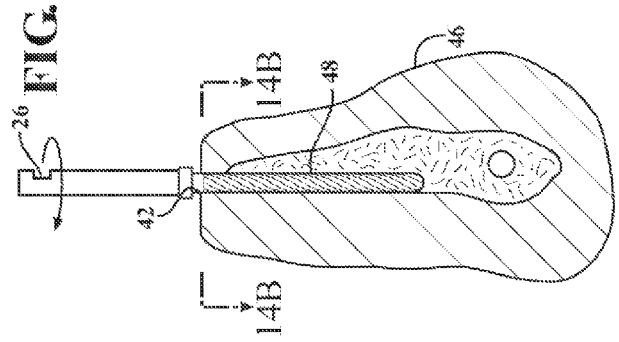

FLUTED OSTEOTOME AND SURGICAL METHOD FOR USE

CROSS REFERENCE TO RELATED APPLICATIONS

This application is a continuation of U.S. Ser. No. 13/608,307 filed Sep. 10, 2012, which is a continuation-in-part of U.S. Ser. No. 13/427,391 filed Mar. 22, 2012, which claims priority to Provisional Patent Application No. 61/466,579 filed Mar. 23, 2011, the entire disclosures of each are hereby incorporated by reference and relied upon.

BACKGROUND OF THE INVENTION

Field of the Invention

The invention relates generally to osteotomes, and more particularly to surgical methods for expanding an initial osteotomy to receive an implant.

Related Art

An implant is a medical device manufactured to replace a missing biological structure, support a damaged biological structure, or enhance an existing biological structure. Bone implants are implants of the type placed into the bone of a patient. Bone implants may be found throughout the human skeletal system, including dental implants in a jaw bone to replace a lost or damaged tooth, joint implants to replace a damaged joints such as hips and knees, and reinforcement implants installed to repair fractures and remediate other deficiencies, to name but a few. The placement of an implant often requires a preparation into the bone using either hand osteotomes or precision drills with highly regulated speed to prevent burning or pressure necrosis of the bone. After a variable amount of time to allow the bone to grow on to the surface of the implant (or in some cases to a fixture portion of an implant), sufficient healing will enable a patient to start rehabilitation therapy or return to normal use or perhaps the placement of a restoration or other attachment feature.

The present invention is directed toward the preparation of a bone implant in cases where expansion of an initial osteotomy is required. A dental implant is shown in FIG. 1 for exemplary purposes as illustrative of the preparation steps customary in many bone implant applications. According to current techniques, at edentulous (without teeth) jaw sites that need expansion, a pilot hole is bored into the recipient bone to form the initial osteotomy, taking care to avoid the vital structures. The pilot hole is then expanded using progressively wider expander devices called osteotomes, manually advanced by the surgeon (typically between three and seven successive expanding steps, depending on implant width and length). See for example FIG. 2. Once the receiving hole has been properly prepared, a fixture screw (usually self-tapping) is screwed into place at a precise torque so as not to overload the surrounding bone.

The osteotome technique has become widely utilized in situations requiring preparation of an osteotomy site by expansion of a pilot hole. By nature, the osteotome technique is a traumatic procedure. The instruments are advanced with the impact of a surgical mallet, which compacts and expands the bone in the process of preparing osteotomy sites that will allow implant placement. (FIG. 2.) Treatment of a mandibular site, for example, is often limited due to the increased density and reduced plasticity exhibited by the bone in this region. Other non-dental bone implant sites may have similar challenging density and plasticity characteristics. Additionally, since the osteotome is inserted by hammering, the explosive nature of the percussive force provides limited control over the expansion process, which often leads to unintentional displacement or fracture of the labial plate of bone in dental applications. Many patients do not tolerate the osteotome technique well, frequently complaining about the impact from the surgical mallet. In addition, reports have documented the development of a variety of complications that result from the percussive trauma in dental applications, including vertigo and the eyes may show nystagmus (i.e., constant involuntary cyclical movement of the eyeball in any direction).

More recently, a technique has been developed for dental applications that allow the atraumatic preparation of implant sites by eliminating the use of a surgical mallet. This procedure is based on the use of a ridge expansion system that includes a bur kit and instruments known as motor-driven bone expanders, such as those marketed by Meisinger split control bone management system (Neuss, Germany). First a pilot hole is drilled at the implant site, then a series of progressively larger expander screw taps are introduced into the bone by hand or with motor-driven rotation, which decreases surgical trauma (as compared with hammer taps) while providing superior control over the expansion site. See for example FIG. 3. The thread pattern of the expander screw taps has been designed to compact bone laterally as the instrument advances into the osseous crest. This system allows expansion and preparation of implant sites in Type II and III bone, as well as compaction of Type IV bone. The Meisinger split control bone management system may be implemented with a so-called "expander bur" tool to prepare the initial pilot hole to receive the first expander screw tap. In dentistry, the term "bur" is usually synonymous with "cutter." The expander bur tool apparently grinds a taper on the inner wall of the pilot hole osteotomy that will readily accept the tapered shape of the first expander screw tap.

Since they are operated with an electric hand piece, the expander screw taps can be utilized in the anterior as well as posterior regions without impingement of the facial tissues or the positional limitations imposed by traditional osteotomes (unlike a more traditional mallet-driven osteotome which cannot easily reach for example the lower mandible posterior). Furthermore, the rotational control of the expansion permits treatment of the mandibular atrophic ridge. The system can be utilized by itself or with osteotomes and surgical drills to assist in the placement of a variety of implant design.

US Publication No. 2006/0121415 to Anitua Aldecoa describes the use of motor-driven tools and methods for expanding a human bone for the purpose of installing a dental implant. Similar to the progressive illustration shown in FIG. 3, a starter drill is used to create a pilot hole followed by the insertion of an expander screw tap type osteotome having a conical/cylindrical geometry with progressive cross-section. A surgical motor is used to rotate the osteotome at relatively low speeds. Another example of this technique is described in U.S. Pat. No. 7,241,144 to Nilo et al, issued Jul. 10, 2007. The entire disclosures of US Publication No. 2006/0121415 and U.S. Pat. No. 7,241,144 are hereby incorporated by reference.

In the prior art designs involving motor-driven bone expansion, the rotary speed of the expander screw tap is locked in a fixed relationship to the expansion rate of the osteotomy. This is because the expander tap threads cut into the bone and advance the expander tap deeper into the initial osteotomy with rotation. The "root" of the expander screw tap does the expanding work while vertical advance is controlled by pitch of threads and rotation speed. In other words, the thread pitch of the expander screw tap combined with its taper angle is fixed and cannot be altered by the surgeon. If a surgeon wishes to expand the bone more slowly, the only recourse is to turn the expander more slowly. Conversely, if they wish to expand the bone more rapidly, the only option is to turn the expander tool more quickly. Thus, the rate of bone expansion is a direct and unalterable function of the rate at which the surgeon turns the expander tool, and the surgeon is unable to vary other parameters such as pressure and/or rotation rate to achieve an optimum expansion rate.

The utilization of motor-driven bone expanders served in the past (FIG. 3) as an innovative technique offering an atraumatic alternative to the traditional mallet-driven osteotomes (FIG. 2). These instruments also provide, at least arguably, a favorable increase in the control of the bone expansion, which facilitates implant-site preparation while allowing universal intraoral use. Nevertheless, there are many shortcomings of the present motor-driven bone expander screw tap techniques. These shortcomings include a relatively large number of intermediate progressive expansions steps due to the surgeon's inability to disassociate the tool rotation rate from the bone expansion rate. A typical osteotomy kit for dental applications may include 4-6 expander screw taps which make the kit cost relatively expensive. Another disadvantage is that each expander screw tap takes time to install and perhaps an equal amount of time to remove (i.e., un-screw). Because of the relatively large number of progressive expansions steps needed, this translates to a long surgical procedure which increases patient discomfort and procedure cost. Yet another disadvantage is that each rotary expansion step introduces some degree of error into the osteotomy. In dental applications for example, the surgeon's hand controlling the advancing expander screw tap is typically located outside the patient's mouth, which is laterally offset from the rotational axis of the expander tap. Thus, even though a surgical motor may be used to drive the expander tap, there is a very real possibility that the surgeon will introduce the some tilt or wobble inadvertently as the expander tap is advanced (or withdrawn) thus distorting the intended shape of the osteotomy or even worse provoking a lateral fracture in the bone.

This inexorable linking of tool rotation rate to bone expansion rate in all prior art rotary expander systems limits surgical control over the implant process, and in some cases may lead to unnecessary patient discomfort. There is therefore a need in the art for an improved surgical method for expanding an initial osteotomy to receive an implant in all bone applications, and tools therefor, that provide greater surgical control, are less costly, less likely to introduce error and that reduce patient discomfort.

SUMMARY OF THE INVENTION

According to a first aspect of this invention, a surgical method is provides for expanding an initial osteotomy to receive a bone implant. An osteotome is provided having a tapered working end. The tapered working end of the osteotome is inserted into an initial osteotomy. The initial osteotomy has an interior surface surrounded by bone. The initial osteotomy is enlarged by forcibly advancing the osteotome into the initial osseotomy. The inserting and enlarging steps are repeated, as needed, with progressively larger tapered osteotomes until an osteotomy of predetermined size is achieved. The invention is distinguished by the working end of the tapered osteotome having one or more longitudinally extending burnishing edges. The enlarging step includes simultaneously rotating and pushing the working end of the tapered osteotome into the osteotomy so that the one or more burnishing edges concentrate the pushing and rotational force through the burnishing edge in outward normal and tangential component forces against the interior surface of the osteotomy to incrementally expand the osteotomy with little to no removal of bone material.

According to a second aspect of the invention, a surgical method is provided for expanding an initial osteotomy to receive a bone implant. An osteotome is provided having an upper end and a tapered working end. The working end of the tapered osteotome has one or more longitudinally extending burnishing edges. The upper end of the osteotome is locked in a drill motor and then rotated in a first rotary direction. The tapered working end of the osteotome is inserted into an initial osteotomy having an interior surface surrounded by bone. The initial osteotomy is then enlarged by pushing the working end of the tapered osteotome into the initial osteotomy and simultaneously rotating the osteotome in the first rotary direction so that the one or more burnishing edges cut against the interior surface of the osteotomy to expand the osteotomy by removal of bone material. Following this, the locking and the inserting and the enlarging steps are repeated but with a second larger tapered osteotome. The second larger osteotome is rotated in a second rotary direction by the drill motor which is reverse of the first rotary direction which has the effect of concentrating the pushing and rotational force through the burnishing edge in outward normal and tangential component forces against the interior surface of the osteotomy to incrementally expand the osteotomy with little to no removal of bone material.

Burnishing is the deformation of a surface due to stressed contact with another object. Burnishing is commonly used in metalworking as a cold forming process, without actual removal of metal, where a tool is rubbed on the metal surface of the part with sufficient force to cause plastic flowing of the metal. The technique of burnishing is not commonly applied in the bone arts, and is heretofore not been applied in surgical procedures to expand an initial osteotomy for the purpose of receiving a bone implant.

This invention overcomes the disadvantages and shortcomings of prior art osteotome techniques offering an atraumatic alternative to the traditional mallet-driven osteotomes without any disadvantages of rotary expander screw tap systems. The present surgical method provides a highly controllable, relatively fast and effective technique for expanding an initial osteotomy to receive a bone implant. By forcibly rubbing the burnishing edges of the osteotome against the interior surfaces of the osteotomy, the bone material is effectively expanded and simultaneously compressed without creating excessive heat or trauma to the bone material. By simply rotating the osteotome in the opposite rotary direction, the tool can be made to expand by cutting. Because the concepts of this invention de-link rotation rate of the tool to the bone expansion rate, the surgeon is provided with substantially greater control which reduces the possibility for the introduction of inadvertent lateral forces prevalent with prior art expander screw tap devices. Surgical procedures according to the present methods can be carried out over less time, thereby resulting in less trauma and discomfort for the patient.

BRIEF DESCRIPTION OF THE DRAWINGS

These and other features and advantages of the present invention will become more readily appreciated when considered in connection with the following detailed description and appended drawings, wherein:

FIG. 4 is a perspective view of an osteotome according to one embodiment of the present invention;

FIG. 5 is a side elevation view of the osteotome shown in FIG. 4;

FIG. 6 is a cross-sectional view through the working end of the osteotome as taken generally along lines 6-6 in FIG. 5;

FIG. 9 is a fragmentary perspective view showing the working end of an osteotome according to one embodiment of this invention having six straight flutes;

FIG. 10 is a fragmentary perspective view of an alternative osteotome configuration according to this invention wherein the working end is configured with ten spiral flutes;

FIG. 14A is a simplified cross-sectional view through a bone prepared for surgical expansion with a pilot drill having created an initial osteotomy site;

FIG. 14B is a view taken generally along lines 14B-14B in FIG. 14A;

FIG. 15A is a simplified surgical procedure showing a progression from that of FIG. 14A with a first osteotome having been inserted into the initial osteotomy to expand the initial osteotomy into a first expanded osteotomy;

FIG. 15B is a view taken generally along lines 15B-15B of FIG. 15A;

FIG. 16A shows a further progression in the surgical procedure from that of FIG. 15A in which a second osteotome is inserted into the osteotomy and operated in a manner so as to expand the osteotomy further;

FIG. 16B is a view as taken generally along lines 16B-16B in FIG. 16A;

DETAILED DESCRIPTION OF THE PREFERRED EMBODIMENT

Figure 1:
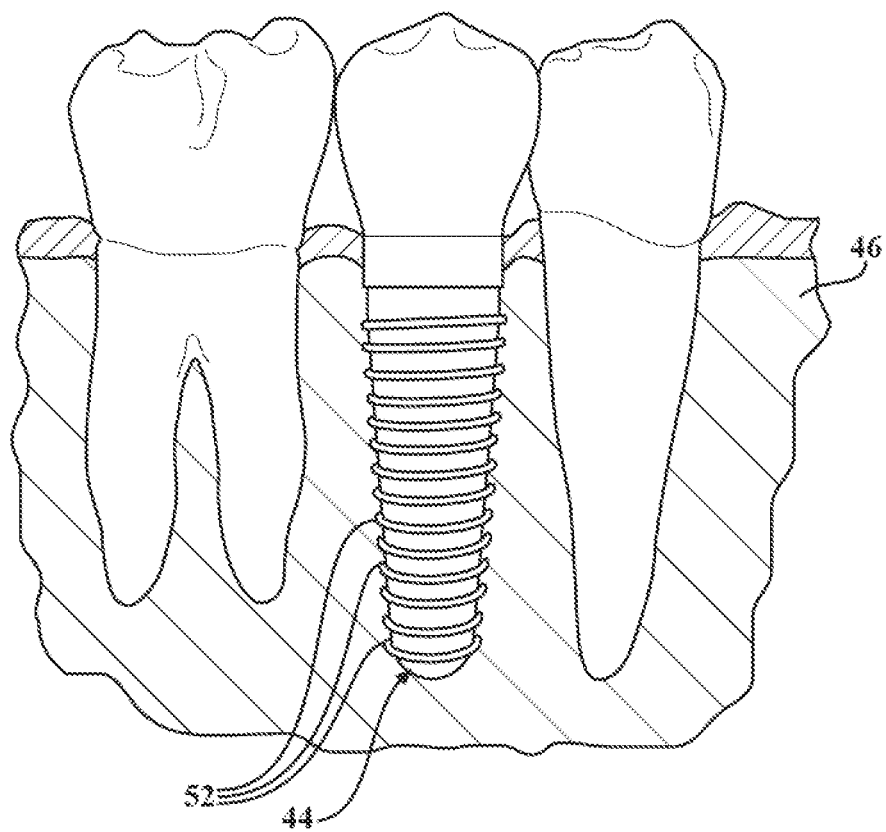
FIG. 1 is a modified cross-sectional view through jawbone showing an exemplary dental implant in bone composed of a lower fixture portion and an upper restoration, the dental implant being flanked on either side by natural teeth.

Referring to the figures wherein like numerals indicate like or corresponding parts throughout the several views, a burnishing osteotome according to the present invention is generally shown at 22 in FIGS. 4-11 and 13. The osteotome 22 comprises a longitudinally extending shank 24. The shank 24 has a coupling 26 at one end thereof to attach to a rotary input such as from a surgical motor having speed and torque controls. The osteotome 22 also includes a working end 28. The working end 28 extends longitudinally from the shank 24 opposite the coupling 26. For dental applications as one example, the working end 28 may have a length of approximately 11-15 mm, although longer or shorter lengths may also be fashioned to suit the application. As perhaps best shown in FIG. 5, the working end 28 has a taper along at least a portion of its length. A leading distal tip 30 of the working end 28 defines a minimal outer diameter, and an upper end 32 defines a maximum outer diameter of the tapered portion. For dental applications, the difference between the minimal outer diameter (at 30) and the maximum outer diameter (at 32) is preferably 1 mm, although larger or smaller differences can be achieved with larger or smaller taper angles. Of course, for non-dental applications involving larger bone osteotomy sites, the dimensional scale of the osteotome 22 will typically be much larger.

Figure 7:
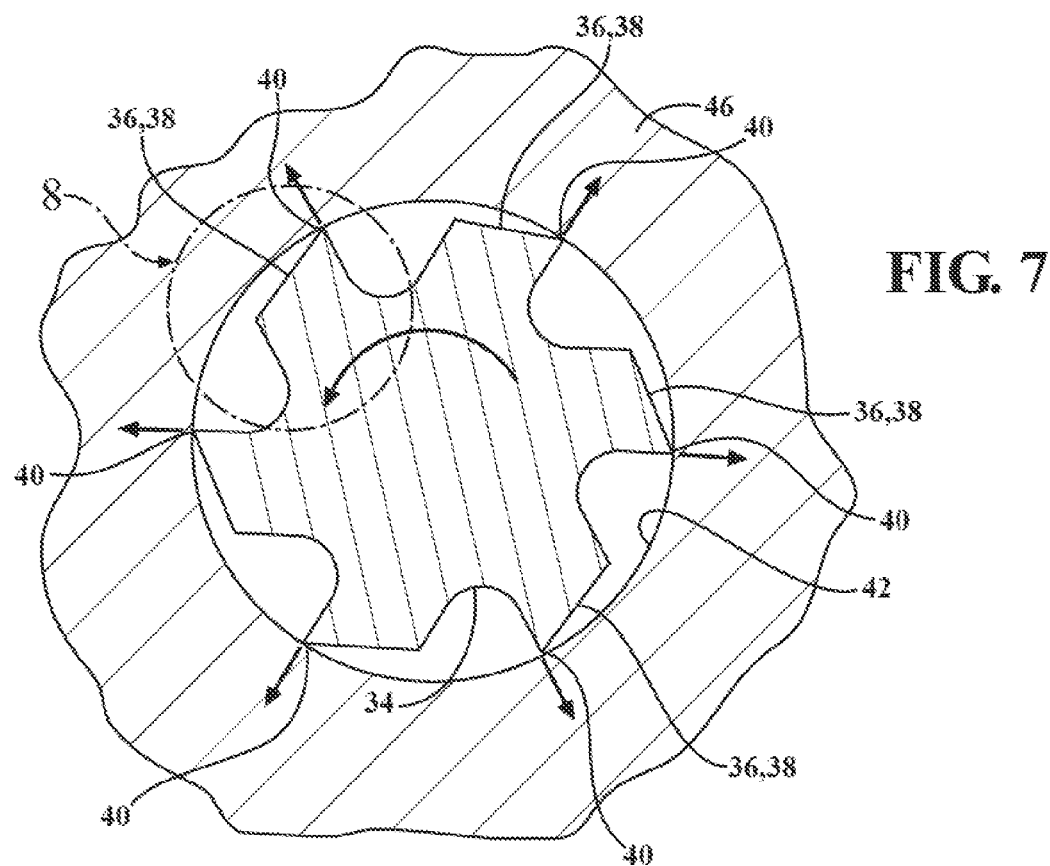
FIG. 7 is a cross-sectional view through the working end of an osteotome as taken generally along lines 6-6 in FIG. 5 but looking the other direction which, in use, is downwardly into an osteotomy, with radial lines emanating from the burnishing edges of the osteotome to indicate laterally outward expansive forces applied through the burnishing edges to the interior surface of an osteotomy.
Figure 8:
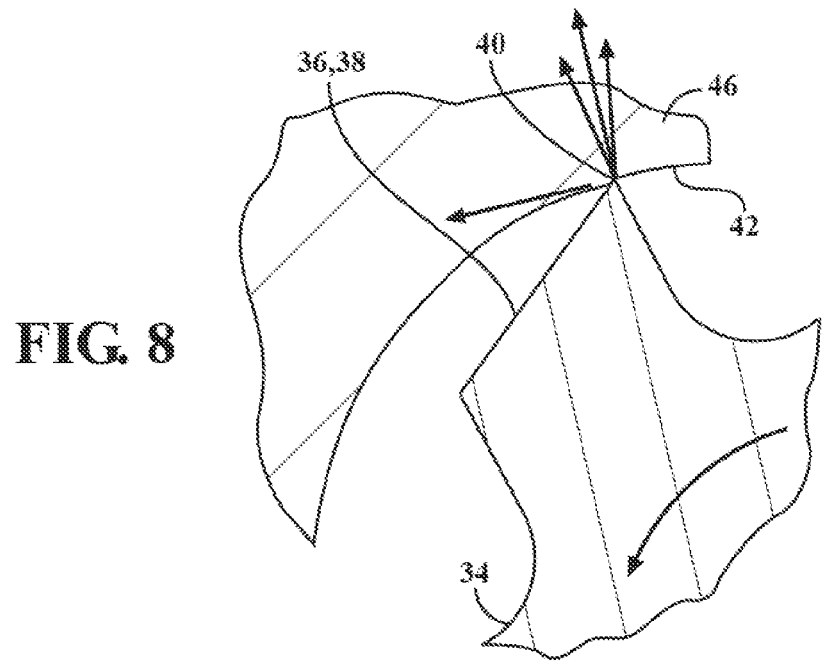
FIG. 8 is an enlarged view of the area circumscribed at 8 in FIG. 7 and depicting the interaction between the burnishing edge of the flute of the osteotome and the interior surface of the osteotomy, with radial and longitudinal forces indicated by arrows.

Referring now to the cross-sectional views of FIGS. 6-8, the working end 28 is shown including a root shaft 34, from which at least one, but more preferably a plurality of flutes 36 extend. The plurality of flutes 36 may comprise at least three flutes 36. Preferably, the plurality of flutes 36 are equally circumferentially spaced from one another so that if for example there are four flutes 36 they are arranged 90° apart; six flutes 36 would be arranged 60° apart; eight flutes 36 would be arranged 45° apart; ten flutes 36 would be arranged 36° apart; and so on. The number of flutes 36 may be dictated for primarily practical reasons by the size of the osteotome 22, such that very small diameter osteotomes 22 have the fewest number of flutes 36 and progressively larger osteotomes 22 have progressively more flutes 36.

Each flute 36 extends radially outwardly to a crest 38 which defines the major diameter of the working end 28 as a function of length. That is, because the working end 28 is tapered, its diameter changes along its length. Therefore the major diameter adjacent the distal tip 30 will be smaller than the major diameter adjacent the upper end 32. Thus, the major diameter is a function of length measured as it were from the distal tip 30. As perhaps best shown in FIG. 8, a longitudinally extending burnishing edge 40 is disposed along the outermost portion of the crest 38. The burnishing edge 40 is that specific portion of the crest 38 which lies along the major diameter of the tapered working end 28. In the embodiments illustrated in the drawing figures, the burnishing edge 40 in each instance is non-rotatably fixed relative to the root shaft 34. In applications such as dentistry where the relatively small osteotome sizes introduce practical manufacturing constraints, the burnishing edge 40 may take the form of a fixed ridge that is unitary (monolithic) with the flutes 36 and entire working end 28 of the osteotome 22. However, if manufacturing techniques and other practical constraints permitted, the burnishing edge 40 could be formed by a roller element in order to reduce friction and better manage heat build-up.

Returning again to FIG. 8, the crest 38 is shown as establishing a large negative rake angle leading up to the burnishing edge 40. A rake is an angle of slope measured from the leading face of the tool (the crest 38 in this case) to an imaginary line extending perpendicular to the surface of the worked object (e.g., inner bone surface of the osteotomy). Rake angle is a parameter used in various cutting and machining processes, describing the angle of the cutting face relative to the work. There are three types of rake angles used in metal working: positive, negative, and zero. However, in the preferred embodiment of this present application of a burnishing technique, a negative rake angle is employed, and more preferably a large negative rake angle. While the actual angle of the negative rake is adaptable to suit the particular specifications, including the relative roundness or sharpness of the burnishing edge 40, negative rake angles greater than about 45°, and even more preferably greater than 60°, have been found to produce satisfactory results. The large negative rake angle of the present osteotome 22 applies outward pressure at the burnishing edge 40 to create a compression wave ahead of the point of contact, loosely akin to spreading butter on toast. Downward pressure applied by the surgeon is needed to keep the burnishing edge 40 in contact with the bone surface of the osteotomy being expanded, that is, to keep it pushing on the compression wave. This is aided by the taper effect of the osteotomy and tool 22 to create lateral pressure (i.e., in the intended direction of expansion). The harder the surgeon pushes down, the more pressure is exerted laterally. This gives the surgeon complete control of the expansion rate irrespective to a large degree on the rotation speed of the osteotome 22. Thus, the burnishing effect's intensity depends on the amount of force exerted on the osteotome 22. The more force exerted, the quicker expansion will occur As shown in the enlarged and somewhat exaggerated for clarity FIG. 8, as the burnishing edge 40 drags across the bone, the force on the burnishing edge 40 can be decomposed into two component forces: one normal to the bone's surface, pressing it outwardly, and the other tangential, dragging it along the inner surface of the osteotomy. As the tangential component is increased, the burnishing edge 40 will start to slide along the bone. At the same time, the normal force will deform the softer bone material. If the normal force is low, the burnishing edge 40 will rub against the bone but not permanently alter its surface. The rubbing action will create friction and heat, but this can be controlled by the surgeon by altering, on-the-fly, the rotation speed and/or pressure and/or irrigation flow. As will be described subsequently in connection with FIG. 20, because the working end 28 of the osteotome 22 is tapered, the surgeon may at any instant during the surgical procedure lift the burnishing edges 40 away from contact with the surface of the bone to allow air cooling and/or irrigation. This can be done in a controlled "bouncing" fashion where pressure is applied in short bursts with the surgeon continuously monitoring progress and making fine corrections and adjustments. Conversely, as the normal force increases, eventually the stresses in the bone's surface exceed its yield strength. When this happens, the burnishing edge 40 will plow through the surface and create a trough behind it. The plowing action of the burnishing edge 40 thus progressively enlarges the osteotomy. While the elastic properties of bone are well-known, if the load imposed exceeds the bone's ability to deform elastically, it will deform further and change shape permanently by plastic deformation. The permanent change in shape is believed to be associated with micro-cracks that allow energy release, a compromise that is a natural defense against complete fracture. If these micro-cracks are small, the bone remains in one piece while the osteotomy expands.

Expansion of the osteotomy occurs when the burnishing edge 40 is rotated against the bone surface of the osteotomy and downward pressure is applied by the surgeon. This has the effect of causing, at the same time, rotation and translation of the burnishing edge 40, but in a manner that does not positively link rotation and translation as in prior art expander screw tap devices. The osteotomy, therefore, is formed into the final size ready to receive the fixture portion of an implant by a series of small incremental plastic deformations created by sweeps of successive burnishing edges 40 pressed hard against the interior surface of the osteotomy. Each such plastic deformation is followed by a short interval of rest before the arrival of the next successive burnishing edge 40. Additional discussion concerning the effects of burnishing on the bone structure is described below in connection with FIGS. 24A-D.

The burnishing edge 40 is shown in FIG. 8 comprising a chisel-like shape held at the previously described large negative rake angle. However, those of skill will appreciate that the burnishing edge 40 could be formed by other crest 38 profile shapes, such as rounded or lobed designs, provided the manufacturing techniques required to make such an alternative profile were found to be cost-justified in comparison with that of the profile as shown in FIGS. 7 and 8. Furthermore, as described below in connection with FIG. 23, the chisel-like shape of the preferred embodiment is useful as a cutting tool when rotated in reverse direction.

Figure 11:
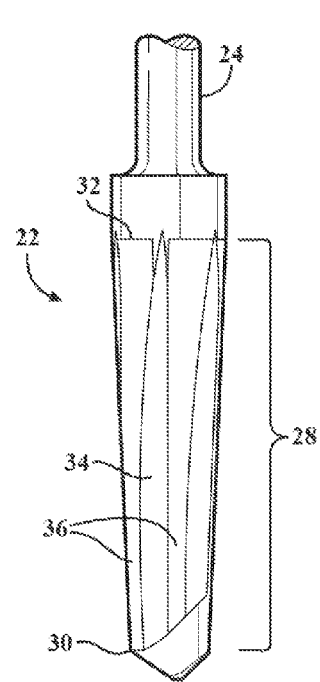
FIG. 11 is a front elevation view of an osteotome embodiment according to this invention including six straight flutes.
Figure 12:
FIG. 12 is a front elevation view of a prior art osteotome of the mallet-driven type shown for comparison purposes adjacent to the osteotome of FIG. 11.
Figure 13:
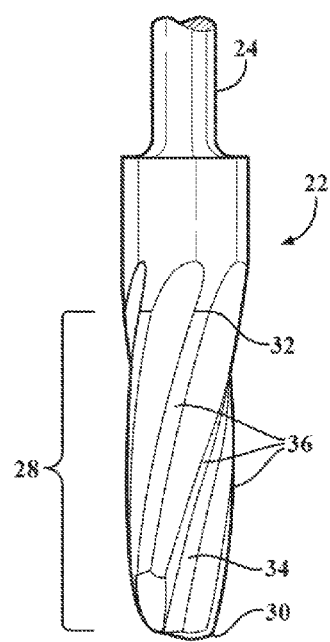
FIG. 13 is a front elevation view of an alternative embodiment of an osteotome according to the subject invention including six helically spiraling flutes shown for comparison purposes adjacent the prior art osteotome of FIG. 12.

Turning now to FIGS. 9-13, the illustrations depict various embodiment in which the flutes 36, and thus by extension the burnishing edges 40, may be formed either with no twist, i.e., straight as in FIGS. 9 and 11, or with a spiral twist along the length of the working end 28 as in FIGS. 10 and 13. A prior art osteotome of the mallet-driven type is shown for side-by-side comparison purposes in FIG. 12. The spiraling direction of the flutes 36 can be set to either wipe against the walls of the osteotomy in an upward motion when rotated in a clockwise direction or a downward direction when rotated in a clockwise direction. The osteotomes 22 shown in FIGS. 22 and 24A-D, for example, are arranged with flute 36 spirals that tend to wipe against the walls of the osteotomy in an upward motion when rotated in a counter-clockwise (burnishing) direction.

By way of example, FIGS. 14A-20 depict a progression of surgical steps for expanding an initial osteotomy 42 to receive a dental implant 44. Although a dental example is used in FIGS. 14A-20 and 22, it must be appreciated that the present invention can be used in non-dental surgical procedures, such as those applied by orthopedic surgeons and perhaps any other procedure requiring creation or enlargement of an osteotomy site with the beneficial bone densification attributes of the present invention. Typically as a first step an initial osteotomy site is prepared by exposing bone 46, and then drilling a pilot hole into the bone 46 with a pilot drill 48. This is shown in FIG. 14A, and may be accomplished with a typical prior art surgical pilot drill 48 turned in a standard clockwise direction. The pilot hole in this instance comprises the initial osteotomy 42. In some cases, the surgeon may decide it is beneficial to saw a groove 50 along the bone ridge as seen in FIG. 14B. The sawed groove 50 typically intersects the pilot hole 42 along the ridge of the bone 46. The surgeon may decide to first drill the pilot hole and then saw the groove 50, or vice versa, it being understood that the groove 50 is an ancillary surgical feature.

A first osteotome 22 according to the present invention is operatively connected to a surgical motor (not shown) though its coupling 26 feature. Then the working end 28 of the first osteotome 22 is inserted into an initial osteotomy 42. The interior surface of the initial osteotomy 42 is surrounded by bone 46. If the diameter of the pilot drill 48 is, for example 1.5 mm, then preferably the major diameter of the working end 28 of the first osteotome 22 adjacent the leading distal tip 30 is also 1.5 mm so that it follows easily the pilot hole. Because of the widening taper, the major diameter of the working end 28 adjacent the upper end 32 is larger than the initial osteotomy. This may be, for example, 2.5 mm. At these exemplary dimensions, a first osteotome 22 having four equally spaced flutes 36/burnishing edges 40 of straight or helical twist has been found to provide satisfactory results. More or fewer flutes 36/burnishing edges 40 are certainly possible.

The initial osteotomy 42 is enlarged in a next step of the procedure by forcibly advancing the working end 28 of the first osteotome 22 into the initial osseotomy 42 to the desired depth, which is depicted in FIG. 15A. Depth markings in the form of laser-etched stripes may be applied to the working end 28 to indicate customary depths (as measured from the distal tip 30) of, for example, 7 mm, 10 mm, 13 mm and 15 mm. This forcible advancing includes simultaneously rotating and pushing the working end 28 of the first tapered osteotome 22 into the osteotomy 42 so that its one or more burnishing edges 40 concentrate the pushing and rotational force in outward normal and tangential component forces (FIG. 8) against the interior surface of the osteotomy 42. FIG. 15A illustrates a counter-clockwise rotation of the osteotome 22, but that direction is merely preferred and can be reversed with suitable alterations made to the shape and/or rake angle of the osteotome 22. Although the surgeon may vary the rotational speed of the osteotome 22 according to the dictates of the situation in their judgment, experimental results indicate that rotation speeds between about 200-1200 RPM and torque settings between about 15-50 Ncm provide satisfactory results. More preferably rotation speeds between about 600-1000 RPM and torque settings between about 20-45 Ncm provide satisfactory results. And still more preferably, rotation speeds in the range of 800-900 RPM and torque settings of about 35 Ncm provide satisfactory results.

Figure 2:
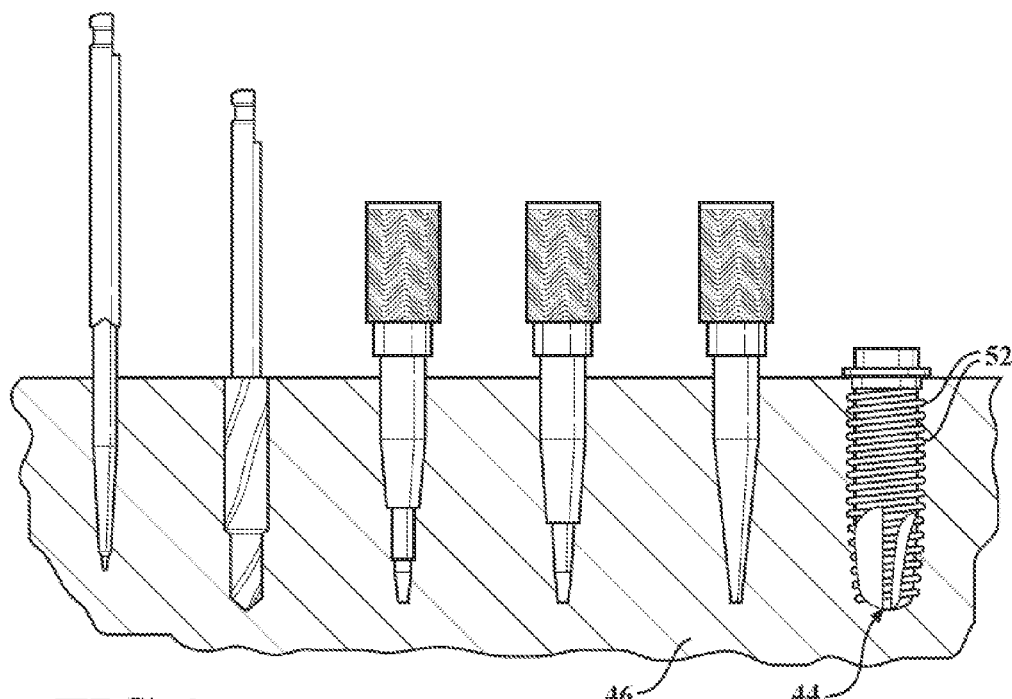
FIG. 2 is a simplified schematic view illustrating a progressive surgical procedure according to the prior art wherein an initial osteotomy is progressively expanded to receive a dental implant using a traditional mallet-driven osteotome technique.
Figure 3:
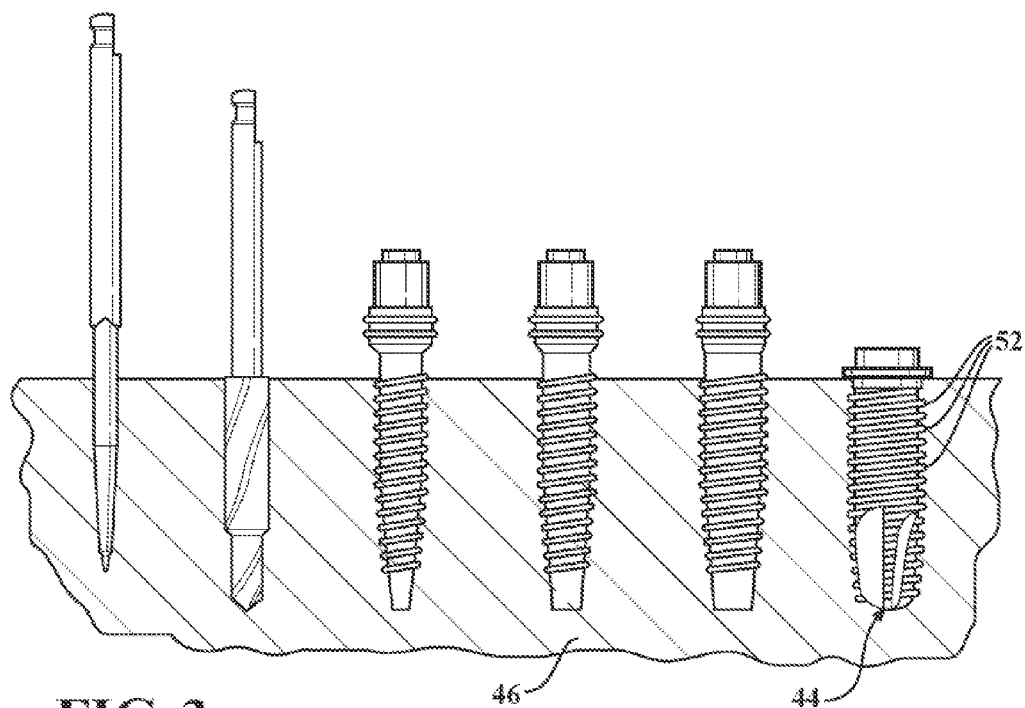
FIG. 3 is a view as in FIG. 2 but showing prior art expander screw tap technique which has seeks to replace the mallet-driven osteotome technique of FIG. 2.
Figure 20:
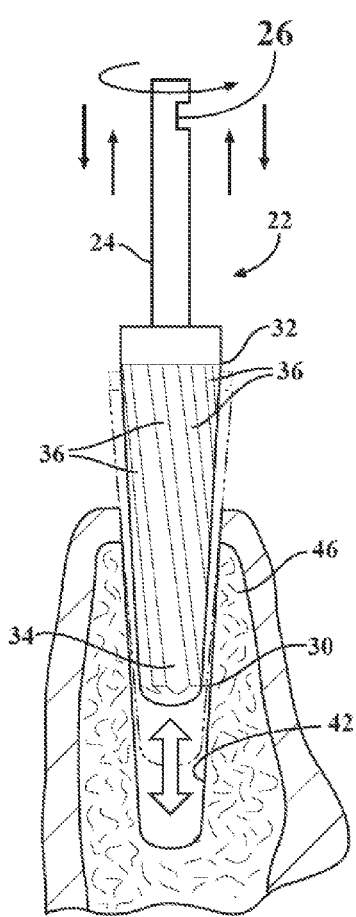
FIG. 20 is a simplified cross-sectional view showing a surgical procedure referred to herein as "bounce" where an osteotome according to the present invention is repeatedly pushed into the osteotomy and withdrawn while the osteotome remains spinning in a repetitive manner so as to enlarge the osteotomy while enabling the surgeon to manage heat build-up and make adjustments on-the-fly.

As perhaps best shown in FIG. 20, the enlarging step may include the controlled practice of bouncing the burnishing edges 40 into and out of contact with the interior surface of the osteotomy 42 while continuously rotating the osteotome 22. This practice is unachievable using prior art osteotome tools and techniques (as shown in FIGS. 2, 3 and 12). However, because the subject osteotome 22 has a tapered working end 22 and only the burnishing edges 40 are in contact with the interior surface of the osteotomy 42, the surgeon may at any time lift the working end 28 out of contact to evaluate progress, manage heat, irrigate, adjust approach, or make other corrections. In fact, the surgeon may practice a very controlled technique whereby the burnishing edges 40 are repeated and successively pushed into and pulled out of the osteotomy 42 in a sort of bouncing maneuver. Although this bouncing technique is not required for proper execution of the method, the novel tool shape and other features of this invention enable the bouncing technique if and whenever the surgeon warrants.

It should also be mentioned that if the surgeon warrants, the osteotome 22 may be rotated in the opposite direction (e.g., clockwise in these examples) and utilize the osteotome 22 to enlarge the osteotomy 42 by cutting or excavating bone material from the osteotomy 42 rather than via compression and plastic deformation. This technique of reversing rotation of the osteotome 22 as an intentional step during the surgical expansion procedure is described more fully below in connection with FIGS. 22 and 23.

When the desired depth (approximately 6-20 mm in dental applications; significantly larger in other medical applications) of the working end 28 has been advanced into the osteotomy, the resultant effect is an incremental expansion of the osteotomy 42 to the dimensions of the working end 28 with little to no removal of bone material 46. The first osteotome 22 is then removed from the osteotomy 42 to reveal a first enlarged osteotomy 42. The first enlarged osteotomy 42 is fully prepared and ready to receive an implant 44 if, in this example with the given dimensions, its fixture portion is sized at about a 3.0 mm diameter.

If the fixture portion of the implant 44 is larger than 3.0 mm (continuing with this dental-specific example for purposes of illustration), then the first enlarged osteotomy 42 must be enlarged still further. This is accomplished by repeating the inserting and enlarging steps with progressively larger tapered osteotomes 22, as needed, until an osteotomy 42 of predetermined size is achieved. More specifically, as shown in FIG. 16A, a second osteotome 22 having a tapered working end 28 that is larger in diameter than the first osteotome 22, is operatively connected to the surgical motor (not shown). The tapered working end 28 of the second osteotome 22 is inserted into the first enlarged osteotomy 42. Using the previously described exemplary dimensions, the major diameter of the working end 28 of the second osteotome 22 adjacent the leading distal tip 30 is 2.5 mm so that it follows easily the first enlarged osteotomy 42.

Because of the widening taper, the major diameter of the working end 28 adjacent upper end 32 is, for example, 3.5 mm. At these exemplary dimensions, the second osteotome 22 having six equally spaced flutes 36/burnishing edges 40 of straight or helical twist has been found to provide satisfactory results. More or fewer flutes 36/burnishing edges 40 are certainly possible.

The surgeon proceeds to further enlarge the first enlarged osteotomy 42 by forcibly advancing the second osteotome 22 into the first enlarged osteotomy 42 to create a second enlarged osteotomy 42. As before, the advancing step is comprised of simultaneously rotating and pushing the working end 28 of the second tapered osteotome 22 to a desired depth into the osteotomy 42 so that its one or more burnishing edges 40 concentrate the pushing and rotational force in outward normal and tangential component forces (FIG. 8) against the interior surface of the osteotomy 42. When the full length (approximately 11-15 mm) of the working end 28 has been advanced into the osteotomy 42, the second osteotome 22 is then removed from the osteotomy 42 to reveal a second enlarged osteotomy 42. The second enlarged osteotomy 42 is fully prepared and ready to receive an implant 44 if, in this example with the given dimensions, its fixture portion is sized at about a 4.0 mm diameter.

Figure 17A:
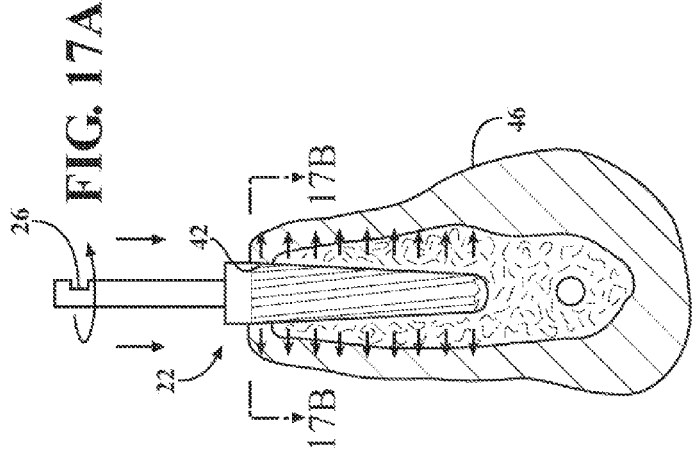
FIGS. 17A and 18A show further progressions in the expansion process from that depicted in FIGS. 14A and 15A and 16A.
Figure 17B:
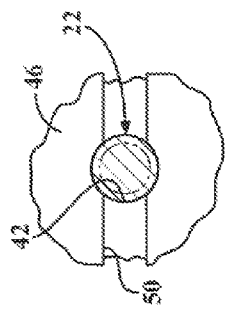
FIGS. 17B and 18B are views taken from lines 17B-17B and 18B-18B in FIGS. 17A and 18A, respectively.

If the fixture portion of the implant 44 is larger than 4.0 mm (continuing with this dental-specific example for purposes of illustration), then the second enlarged osteotomy 42 must be enlarged still further. This is accomplished by repeating the inserting and enlarging steps with a progressively larger tapered osteotome 22. FIG. 17A illustrates this scenario where a third osteotome 22 is operatively connected to the surgical motor. Its tapered working end 28 is inserted into the second enlarged osteotomy 42. Using the previously described exemplary dimensions, the major diameter of the third osteotome 22 adjacent its leading distal tip 30 is 3.5 mm, and adjacent its upper end 32 may, for example, be 4.5 mm. At these exemplary dimensions, the third osteotome 22 may have eight equally spaced flutes 36/burnishing edges 40 of straight or helical twist, although more or fewer flutes 36/burnishing edges 40 are certainly possible.

The surgeon proceeds to further enlarge the osteotomy 42 by simultaneously rotating and pushing the working end 28 of the third tapered osteotome 22 into the osteotomy 42 so that its one or more burnishing edges 40 concentrate the pushing and rotational force in outward normal and tangential component forces (FIG. 8) against the interior surface of the osteotomy 42. When the desired depth (approximately 7-15 mm) of the working end 28 has been advanced into the osteotomy 42, the third osteotome 22 is then removed from the osteotomy 42 to reveal a third enlarged osteotomy 42. The third enlarged osteotomy 42 is fully prepared and ready to receive an implant 44 if, in this example with the given dimensions, its fixture portion is sized at about a 5.0 mm diameter.

Figure 18A:
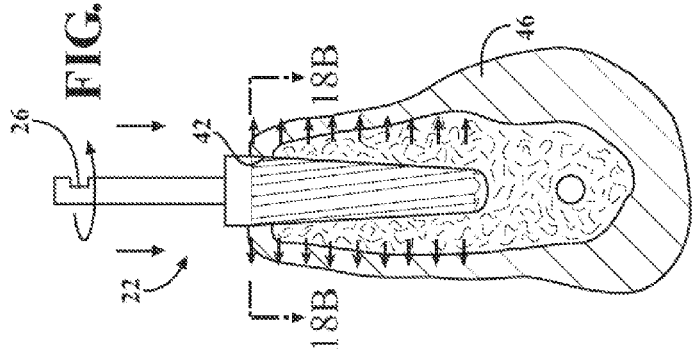
Figure 18B:
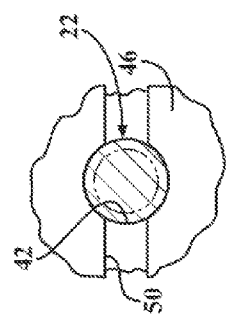

If the fixture portion of the implant 44 is larger than 5.0 mm (continuing with this dental-specific example for purposes of illustration), then the third enlarged osteotomy 42 must be enlarged still further. This is accomplished by repeating the inserting and enlarging steps with a progressively larger tapered osteotome 22. FIG. 18A illustrates use of a fourth osteotome 22 having (for example) a major diameter adjacent its leading distal tip 30 of 4.5 mm, and adjacent its upper end 32 of 5.5 mm. At these exemplary dimensions, the fourth osteotome 22 may have ten equally spaced flutes 36/burnishing edges 40 of straight or helical twist, although more or fewer flutes 36/burnishing edges 40 are certainly possible.

The surgeon proceeds to further enlarge the third enlarged osteotomy 42 by simultaneously rotating and pushing the working end 28 of the fourth tapered osteotome 22 into the osteotomy 42. As before, the one or more burnishing edges 40 concentrate the pushing and rotational forces against the interior surface of the osteotomy 42. When the desired depth (approximately 7-15 mm) of the working end 28 has been advanced into the osteotomy 42, the fourth osteotome 22 is then removed from the osteotomy 42 to reveal a fourth enlarged osteotomy 42. The fourth enlarged osteotomy 42 is fully prepared and ready to receive the implant 44 if, in this example with the given dimensions, the fixture portion is sized at about a 6.0 mm diameter.

Figure 19A:
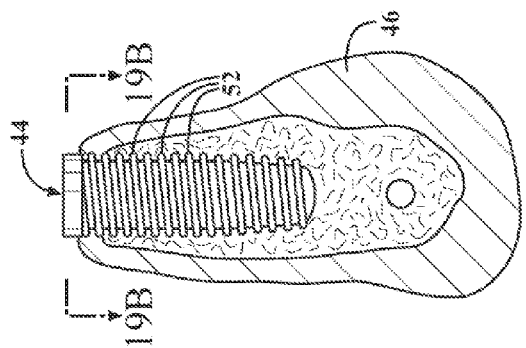
FIG. 19A is a cross-sectional view of the region as in FIG. 18A showing the installation of an implant into the fully enlarged prepared osteotomy.
Figure 19B:
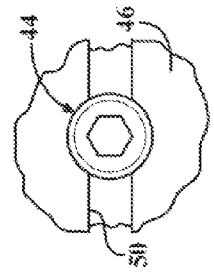
FIG. 19B is a view as taken along lines 19B-19B in FIG. 19A.

To complete the example, FIG. 19A shows the 6.0 mm diameter fixture portion of an implant 44 installed into the fourth enlarged osteotomy 42. The step of installing a fixture portion of an implant 44 includes directly engaging an exterior anchoring thread form 52 of the fixture portion into the expanded osteotomy formed by the burnishing edge 40.

Figure 21:
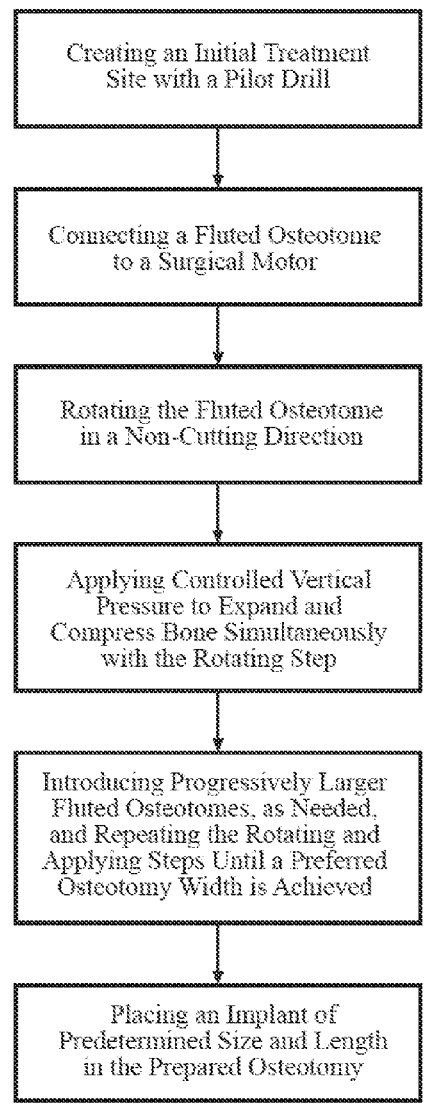
FIG. 21 is a simplified flow chart depicting the primary steps in the subject method.

FIG. 21 provides an exemplary flow diagram of the method of this invention according to one preferred method. The surgical method of this invention, and in particular the diameter to which the osteotomy 42 can be ultimately expanded, is of course limited by the physical properties of the bone 46 and other factors. In other words, the steps of expanding as described herein are directly related to the final desired fixture 44 diameter but also related to the ability of the bone 46 to plastically deform (via the above-described micro-cracks) without fracturing. For example, in some conditions it is not possible for even a skilled surgeon to take a 3 mm width of bone 46 and use the procedures of this invention to expand an osteotomy 42 all the way to 5.5 mm without fracturing the bone 46. However, it may be possible to expand the osteotomy 42 to a slightly smaller 4.5 mm so that it will receive a 5 mm diameter implant 44. Thus, it should be understood that bone's ability to plastically deform without fracturing dictates how much expansion can be achieve, and also dictates at which step the surgeon must to stop the expansion process to avoid fracturing the bone 46 and/or the use of counter-rotation cutting as described below in connection with FIG. 22.

The surgical method of this invention enables an expansion of an initial osteotomy 42 to receive a bone implant 44 that is significantly less traumatic than other prior art osteotome techniques, that is faster than other prior art osteotome techniques, that is able to reach previously difficult to reach areas (e.g., the lower mandible posterior), that requires fewer progressive steps (and tools) to achieve a final enlarged osteotomy than other prior art osteotome techniques, and that is significantly better at managing heat build-up than other prior art osteotome techniques. Heat management is enhanced through irrigation into the osteotomy (difficult with prior art techniques) and also by maintaining a separation space between the root shaft 34 and the bone interior surface of the osteotomy 42. This separation space means less friction and also the opportunity for some degree of convective cooling.

Figure 22:
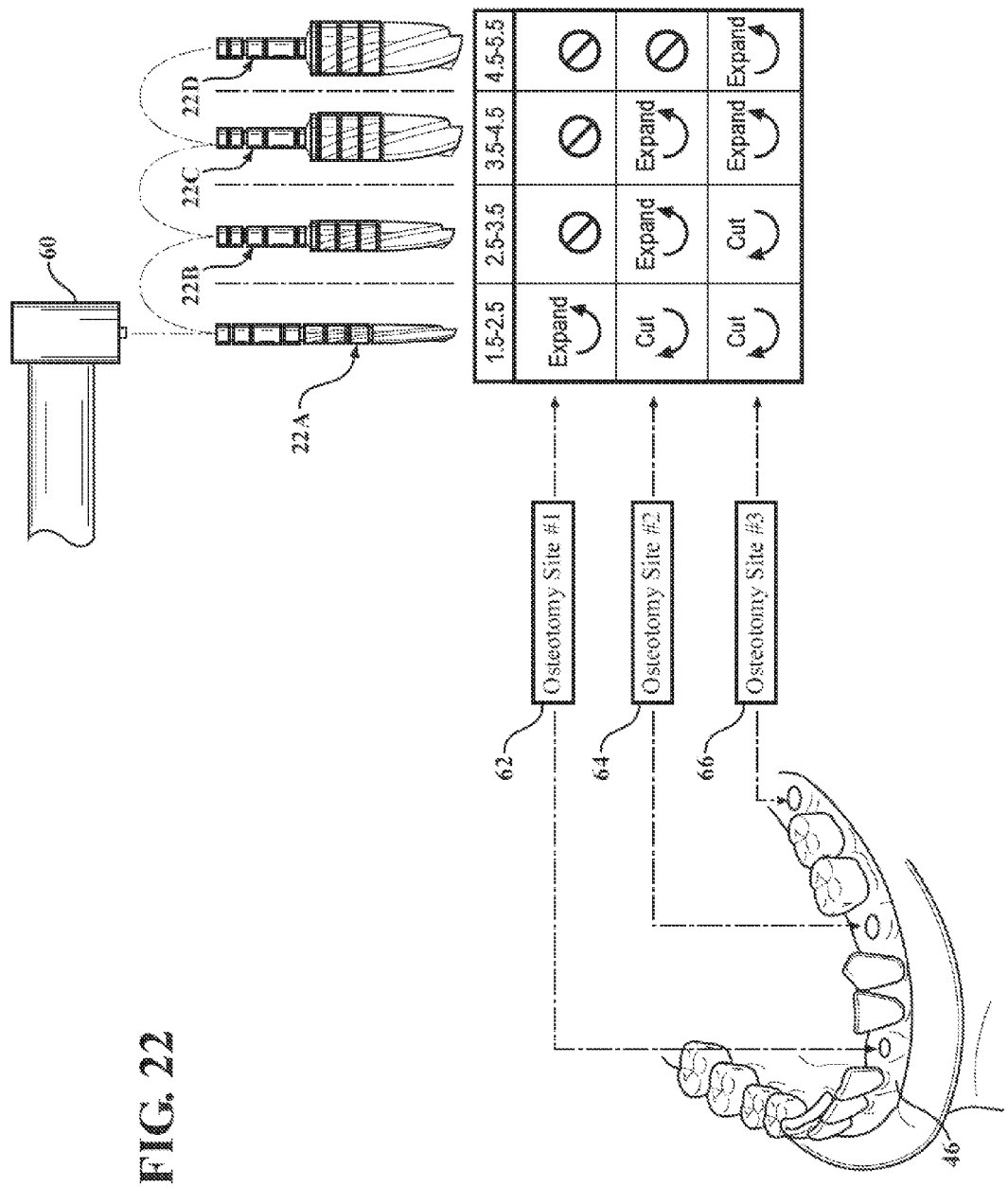
FIG. 22 is a diagrammatic view illustrating by way of example the use of a surgical kit containing four osteotomes of progressively larger diameter according to the present invention in combination with a reversible drill motor to concurrently prepare three separate osteotomy sites in a human jaw using selective reversal of osteotome direction to enlarge each osteotomy either by cutting or burnishing without removing the osteotome from the surgical drill motor.

FIG. 22 is a diagrammatic view illustrating by way of example the use of a surgical kit containing four osteotomes 22A-D of progressively larger diameter according to the present invention in combination with a reversible surgical drill motor 60 to concurrently prepare three separate osteotomy sites 62, 64 and 66, respectively, in a human jaw bone 46 using selective reversal of osteotome direction to enlarge each osteotomy either by cutting or burnishing without removing a given osteotome 22 from the surgical drill motor 60. Although the example is presented here again in the context of a dental application, those of skill in the art will appreciate that the described techniques are adaptable to non-dental applications including, but not limited to, joint replacement and bone fixations generally.

In this example, a first osteotomy site 62 is located in the front of the mandible bone 46 where the bone width is relatively narrow. The composition of the bone 46 in the region of the first osteotomy site 62 may be described as predominantly Type II. A second osteotomy site 64 is located slightly posterior of the first site 62 in a region of the mandible that has moderate bone 46 width. The composition of the bone 46 in the region of the second osteotomy site 64 may be described as generally a combination of Types II and III. A third osteotomy site 66 is located in a molar region of the mandible and is surrounded by a relatively generous bone 46 width. The composition of the bone 46 in the region of the third osteotomy site 66 may be described as predominantly Type III. Due to the varying width and composition of bone 46 at sites 62, 64 and 66, the surgeon does not wish to apply exactly the same technique and procedure to each osteotomy. The novel attributes of the present invention give the surgeon the ability to concurrently prepare all three osteotomy sites 62-66 in different ways.

Figure 23:
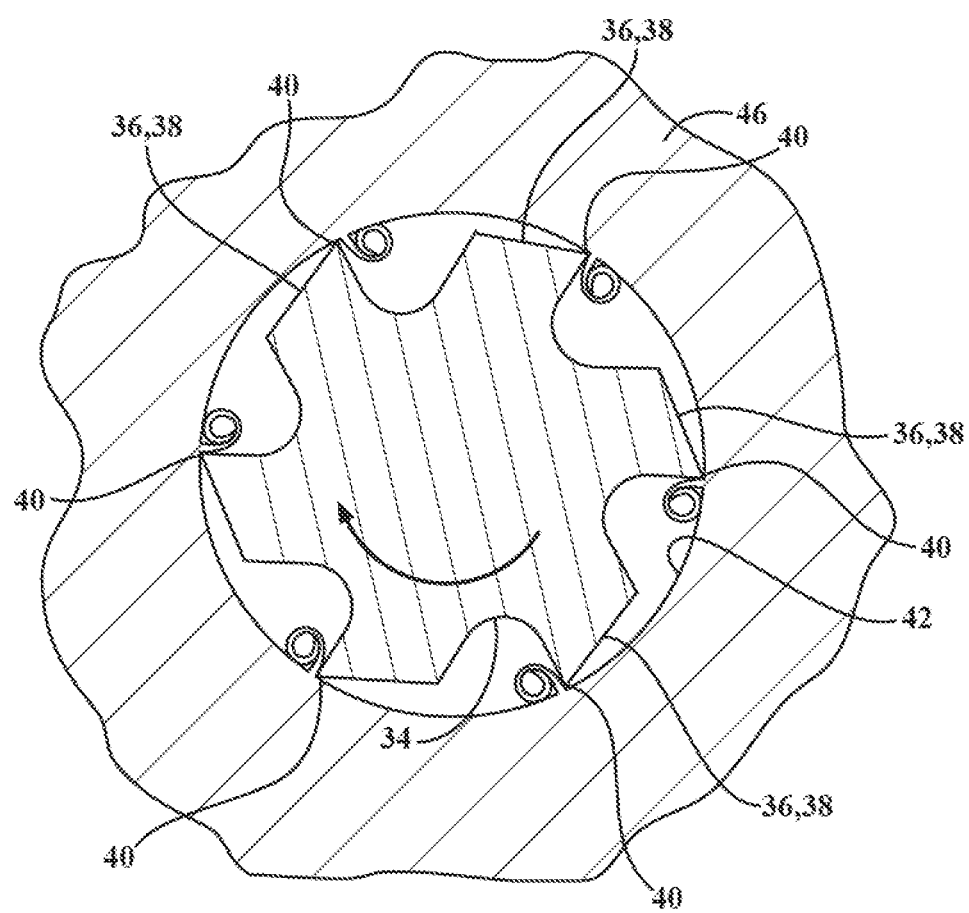
FIG. 23 is a cross-sectional view through the working end of an osteotome as in FIG. 7 but showing a reverse rotational direction to cut the interior surface of the osteotomy (and harvest bone material) rather than burnish.
Figure 24A:
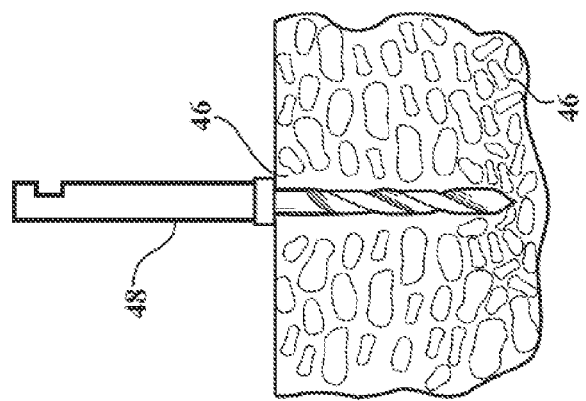
FIGS. 24A-D depict a cross-section through an osteotomy site showing the characteristic cellular structure of bone and the manner in which the bone material surrounding the osteotomy is progressively densified when one pilot drill and three osteotomes of progressively larger diameter according to the present invention are used to enlarge the osteotomy via burnishing.
Figure 24B:
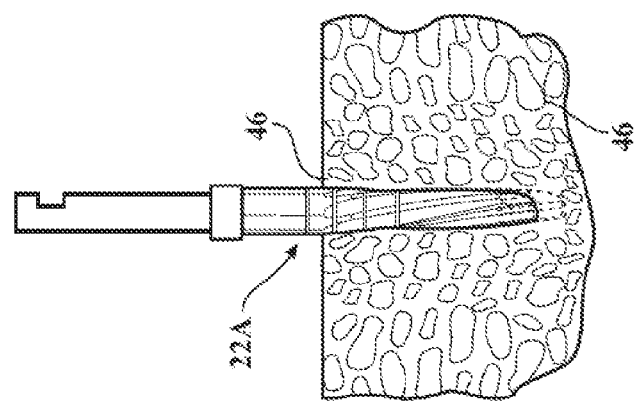
Figure 24C:
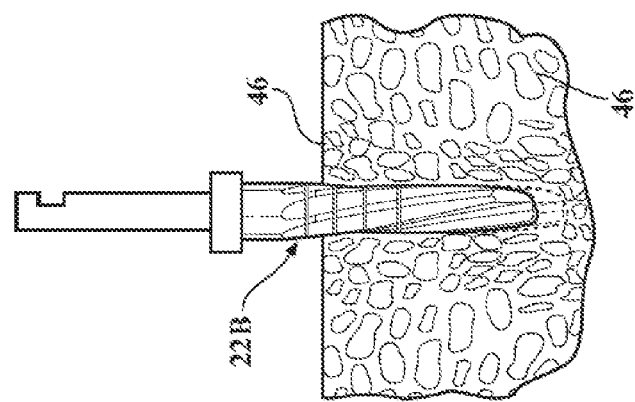
Figure 24D:
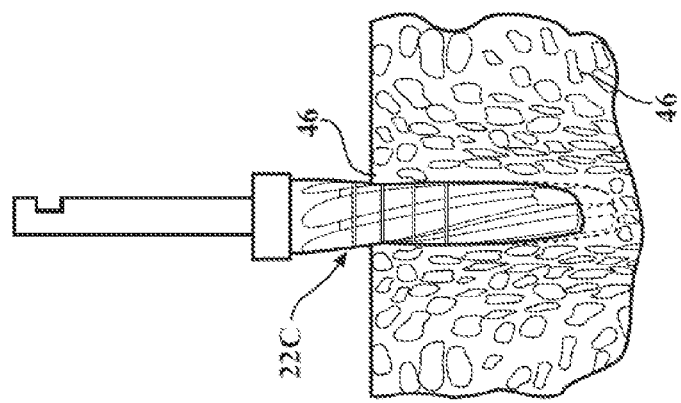

In this example, each osteotomy site 62-66 is presumed to have an initial osteotomy prepared by first drilling a pilot hole of 1.5 mm. (Of course, the circumstances of any given surgical application, whether dental or non-dental in nature, will dictate the size of initial osteotomy and other characteristics of the operation.) The surgeon locks or otherwise installs the first osteotome 22A into the drill motor 60 and sets the rotational direction to counter-clockwise. The surgeon then pushes the first osteotome 22A into the first osteotomy site 62 in the manner described above to expand through burnishing. However, due to the different compositional nature of the second 64 and third 66 osteotomy sites, the surgeon chooses to enlarge by cutting rather than burnishing. To affect this, the surgeon reverses the rotational direction of the drill motor 60 to clockwise without removing the first osteotome 22A from the drill motor 60. Then, using a similar pushing motion, the surgeon enlarges the second 64 and third 66 osteotomy sites by removing bone material which may, if desired, be harvested. FIG. 23 represents a cross-sectional view through the working end of an exemplary osteotome 22 as in FIG. 7, but showing a reverse rotational direction to cut the interior surface of the osteotomy 62 and harvest bone material (shown as chips or shavings in front of burnishing edge 40).

At this stage in the hypothetical example, the first osteotomy site 62 has been expanded as much as the surgeon desires; no further expansion is needed of the first osteotomy site 62. However, the second 64 and third 66 osteotomy sites both require additional expansion. The surgeon then installs the second osteotome 22B into the drill motor 60 and sets the rotational direction to counter-clockwise. Skipping the completed first osteotomy site 62, the surgeon then expands the second osteotome 22B into the second osteotomy site 64 through burnishing in the manner described above. Due to the different compositional nature of the third osteotomy site 66, the surgeon chooses to enlarge by cutting rather than burnishing. To affect this, the surgeon reverses the rotational direction of the surgical motor 60 to clockwise without removing the second osteotome 22B from the surgical motor 60. Then, using a similar pushing motion, the surgeon enlarges the third osteotomy site 66 by removing bone material (which may, if desired, be harvested).

Once the remaining two osteotomy sites 64, 66 have been enlarged by the second osteotome 22B, the surgeon locks or otherwise installs the third osteotome 22C into the drill motor 60 and sets the rotational direction to counter-clockwise. Again skipping the completed first osteotomy site 62, the second 64 and third 66 osteotomy sites are enlarged by burnishing. In both cases, the surgical motor 60 is set to turn in the counter-clockwise direction. The second osteotomy site 64 has now been expanded as much as the surgeon desires; no further expansion is needed of the second osteotomy site 66. However, the third osteotomy site 66 still requires additional expansion. Therefore, the surgeon installs the fourth osteotome 22D into the drill motor 60 and sets the rotational direction to counter-clockwise. Skipping the completed first 62 and second 64 osteotomy sites, the third 66 osteotomy site is enlarged by burnishing using the previously described techniques. Implants (or fixture portions of implants) can now be installed at each osteotomy site 62-66. The surgeon places a 3.0-3.25 mm implant into the first osteotomy site 62, a 5.0 mm implant into the second osteotomy site 64, and a 6.0 mm implant in the third osteotomy site 66.

Those of skill in the art will recognize the substantial improvement in convenience and efficiency the present invention affords by allowing a surgeon to concurrently prepare a plurality of osteotomy sites coupled with the ability to expand one site by burnishing and another site by cutting without removing the osteotome 22 from the drill motor 60. This advantage is of course not exclusive to concurrent multi-site applications, and is in addition to the previously described advantages of significantly reduced trauma, increased speed, improved access to difficult areas, and better heat management.

FIGS. 24A-D depict a cross-section through a typical osteotomy site showing the characteristic cellular structure of bone 46 and the manner in which the bone material surrounding the osteotomy 42 is progressively densified when one pilot drill 48 and three osteotomes 22A-C of progressively larger diameter according to the present invention are used to enlarge the osteotomy 42 via the present burnishing technique.

Bränemark classification of bone includes type I, II, III and IV. Type I is homogeneous compact bone; Type II bone has a thick cortical layer and a dense core; Type III bone has a thin cortical layer and a trabecular core of good strength; Type IV bone has a thin cortical layer and a cancellous core of poor strength. A dense crestal cortex is generally favored for initial fixation of an implant. Often the implant can be placed to take advantage of one or both of the buccal and lingual cortical plates. Placing implants in Type III and IV bone is more challenging that in Types I and II. Moreover, the quality of bone can be extremely variable in a single location. It is likely that at some osteotomy sites the bone 46 may contain voids, fatty marrow, and fibrous inclusion. When the surgeon encounters softer bone texture, the ability to drill accurately diminishes with the loss of tactile sensitivity. Also, inadvertent over-penetration and over-preparation of soft bone is common. Other factors, such as torqueing of the hand piece and reproducing a consistent angle of penetration, become more demanding as bone density decreases.

Use of the present invention to expand an osteotomy by burnishing helps to maintain all of the existing bone 46 material by pushing the bone aside with minimal trauma while developing an accurately shaped osteotomy 42. Compare the progressive expansion shown in FIGS. 24A-24D to note the condensing and compacting cellular structure of the bone 46 as progressively larger osteotomes 22A-C are introduced. In addition, the osseous layer around the osteotomy 42 is compacted, which will form a denser bone interface with the implant 44 and thus improved retention. This benefit is particularly relevant when there is a marginal quantity of bone 46 to start with. It is worth noting that in FIGS. 22 and 24A-D, the spiraling direction of the flutes are set to wipe upwardly against the walls of the osteotomy when rotated in a counter-clockwise (burnishing) direction, and to push chips/debris in a downward direction when rotated in a clockwise (cutting) direction. The spiraling direction of the flutes must be reversed to achieve an opposite reaction when rotating the osteotome 22 in the clockwise and counter-clockwise directions.

Drilling and cutting, by contrast, take bone away from a site. During the drilling process, there is no practical means to immediately improve adjacent bone quality. With the present rotary osteotome technique, the bone layer next to the osteotomy 42 is improved because of the compaction of bone which in turn helps anchor a newly placed implant 44. Drilling does not improve local anatomy or bone quality. The present osteotome 22 is effective to expand the surrounding bone (e.g. in ridge applications) and improve bone quality. The present osteotome 22 techniques offer a useful and predictable procedure, improved tactile sensitivity, improved control, and improved implant placement in soft bone conditions.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A surgical method for enlarging an osteotomy to receive an anchoring screw using continuous high-speed rotation of a bone expander tool, said method comprising the steps of:
providing a bone expander tool having a tapered working end, the working end having a plurality of longitudinally extending blades;
positioning the tapered working end of the bone expander tool so as to enter an osteotomy to be enlarged, the osteotomy having a generally cylindrical or tapered interior surface of bone;
rotating the working end of the bone expander tool at high speed greater than 200 RPM;
pushing the tapered working end into the osteotomy concurrently with said rotating step so that expansion of the osteotomy occurs when the blades incrementally plastically deform the bone while being pressed against the interior surface of the osteotomy, wherein said pushing step includes axially reciprocating the plurality of blades into and out of contact with the interior surface of the osteotomy; and
irrigating the osteotomy concurrently with said pushing step.

2. The surgical method of claim 1, wherein the working end of the bone expander tool includes a plurality of flutes extending from a root shaft, and wherein said pushing step includes maintaining a separation space between the root shaft and the interior surface of the osteotomy as the bone expander tool advances into the depth of the osteotomy.

3. The surgical method of claim 2 wherein the plurality of flutes correspond in number to the plurality of blades, and said pushing step further includes manually applying variable axial pressure.

4. The surgical method of claim 2, wherein the plurality of blades are each defined by a negative rake angle.

5. The surgical method of claim 1, wherein the plurality of blades each have a spiraling twist along the length a length of the working end.

6. The surgical method of claim 1, further including installing an anchoring screw into the expanded osteotomy with thread forms that directly engage into the densified bone surfaces formed by the blades.

7. The surgical method of claim 1, further including the step of preparing an initial osteotomy site by drilling a pilot hole into the bone, the pilot hole comprising the initial osteotomy.

8. A method for expanding the diameter of an osteotomy prior to receiving a bone fixture, said method comprising the steps of:
providing a bone expander tool having a tapered working end, the tapered working end surrounded by a plurality of blades, the blades being configured to cut bone when the tool is rotated in a cutting direction and to outwardly displace bone without cutting when the tool is rotated in an opposite non-cutting direction,
coupling the bone expander tool to a rotary surgical engine,
continuously rotating the tapered working end of the bone expander tool with the surgical engine in the non-cutting direction,
pushing the tapered working end with gentle axial force into a preexisting osteotomy having interior surfaces composed essentially of bone material, said pushing step occurring concurrently with said rotating step but without linking the amount of axial force to the rotation rate of said continuously rotating step, said pushing step including manually pressing the blades against the interior surfaces of the osteotomy; and
irrigating the tapered working end with a cooling saline or water spray concurrently with said continuously rotating and pushing steps so that the blades are irrigated as they press against the interior surfaces of the osteotomy to outwardly displace the bone material in a controlled manner.

9. The method of claim 8, wherein said pushing step includes axially pumping the working end of the bone expander tool so that the blades alternately contact and separate from the interior surface of the osteotomy as the bone expander tool advances deeper into the osteotomy.

10. The method of claim 8, wherein said continuously rotating step includes rotating the working end of the bone expander tool at speeds greater than 200 RPM.

11. The method of claim 8, wherein said continuously rotating step includes applying a torque to the working end of the bone expander tool greater than 15 Ncm.

12. The method of claim 8, wherein the working end of the bone expander tool includes a plurality of flutes extending from a root shaft, and wherein said pushing step includes maintaining a separation space between the root shaft and the interior surface of the osteotomy, wherein the plurality of flutes correspond in number to the plurality of blades, each blade extends radially outwardly to a crest defining the major diameter of the bone expander tool, and wherein the plurality of blades are each defined by a negative rake angle.

13. A surgical method for expanding an osteotomy without hammering, said method comprising the steps of:

providing a rotary osteotome having a tapered working end, the working end having a plurality of longitudinally extending burnishing edges, positioning the tapered working end of the osteotome over an open end of an osteotomy, the osteotomy having an interior surface made of bone, rotating the working end of the osteotome at high speed greater than 200 RPM, pushing the rotating working end into the osteotomy so that the burnishing edges sweep against the interior surface of the osteotomy to expand the osteotomy by incremental plastic deformations that cause a progressive enlargement of the osteotomy beginning adjacent the open end and developing in a frustoconical pattern downwardly into the osteotomy, said pushing step including axially reciprocating the burnishing edges into and out of contact with the interior surface of the osteotomy, and irrigating the osteotomy concurrently with said rotating and pushing steps.

14. A surgical method for enlarging an osteotomy to receive an anchoring screw, said method comprising the steps of:

providing an osteotome having a tapered working end, the working end including a plurality of burnishing edges, positioning the tapered working end of the osteotome so as to enter the osteotomy, the osteotomy having a generally cylindrical or tapered interior surface of bone, and progressively advancing the tapered working end of the osteotome into the osteotomy with an axial pumping motion while continuously rotating the working end so that the burnishing edges intermittently contact the interior surface of the osteotomy with downward pressure to plastically deform the bone interior surface in a radially outward direction.

15. The method of claim 14, further including irrigating the osteotomy concurrently with said progressively advancing step.

16. The method of claim 15, wherein said progressively advancing step includes rotating the tapered working end of the osteotome at speeds greater than 200 RPM, and wherein the rate of axial advance into the osteotomy is independent of the rate of rotation of the working end.

\* \* \* \* \*